(12) United States Patent
Acosta

(10) Patent No.: US 8,926,581 B1
(45) Date of Patent: Jan. 6, 2015

(54) INTERGLUTEAL PERSPIRATION PAD

(71) Applicant: Cesar E. Acosta, El Paso, TX (US)

(72) Inventor: Cesar E. Acosta, El Paso, TX (US)

(*) Notice: Subject to any disclaimer, the term of this patent is extended or adjusted under 35 U.S.C. 154(b) by 145 days.

(21) Appl. No.: 13/778,444

(22) Filed: Feb. 27, 2013

(51) Int. Cl.
*A61F 13/15* (2006.01)
*A41D 13/00* (2006.01)
*A61F 13/66* (2006.01)
*A61F 13/84* (2006.01)

(52) U.S. Cl.
CPC ............ *A41D 13/0002* (2013.01); *A61F 13/66* (2013.01); *A61F 13/84* (2013.01); *A61F 2013/1513* (2013.01)
USPC .......................................... 604/401; 604/402

(58) Field of Classification Search
CPC . A61F 13/66; A61F 13/84; A61F 2013/1513; A61F 2013/15138
USPC .......................... 604/385.01, 385.17, 401, 402
See application file for complete search history.

(56) References Cited

U.S. PATENT DOCUMENTS

| | | | | |
|---|---|---|---|---|
| 2,615,445 A * | 10/1952 | Holmes | ........................ | 128/98.1 |
| 4,484,919 A * | 11/1984 | Sohn et al. | .................... | 604/358 |
| 4,505,707 A * | 3/1985 | Feeney | ............................ | 604/393 |
| 4,932,950 A * | 6/1990 | Johnson | ........................ | 604/392 |
| 5,377,360 A | 1/1995 | Fleitman | | |
| 5,603,653 A | 2/1997 | Hartman | | |
| 5,833,680 A * | 11/1998 | Hartman | .................. | 604/385.17 |
| 6,716,229 B2 * | 4/2004 | Toth | .............................. | 606/197 |
| 6,997,915 B2 | 2/2006 | Gell et al. | | |
| 7,928,279 B2 * | 4/2011 | Rosenberg | ...................... | 602/48 |
| 8,365,737 B2 * | 2/2013 | Mitsui et al. | .................. | 128/830 |

* cited by examiner

*Primary Examiner* — Lynne Anderson
(74) *Attorney, Agent, or Firm* — Crossley Patent Law

(57) ABSTRACT

An intergluteal perspiration pad for wicking perspiration from a gluteal cleft including an absorbent pad having a convex top side configured to conform to a gluteal cleft, a pair of U-shaped first and second ends of the pad, an absorbent cover continuously disposed on the pad, and a pair of U-shaped clip attachment members slidingly disposed through the first and second ends to secure the combined pad and cover to the waistband of various garments.

5 Claims, 3 Drawing Sheets

INTERGLUTEAL PERSPIRATION PAD

BACKGROUND OF THE INVENTION

Various types of personal use absorbent pads are known in the prior art. However, what is needed is an intergluteal perspiration pad which allows one to quickly and conveniently wick perspiration from the gluteal cleft. The present device addresses the foregoing problem by providing an absorbent pad and an absorbent cover thereon with a convex edge configured to conform to the gluteal cleft. In addition, the present device includes a pair of attachment members in the form of U-shaped clips that engage a pair of U-shaped ends of the absorbent pad to secure the device onto a garment waistband in a position to absorb perspiration from the gluteal cleft.

FIELD OF THE INVENTION

The present invention relates to personal use absorbent pads and more particularly, to an intergluteal perspiration pad that wicks perspiration from gluteal cleft.

SUMMARY OF THE INVENTION

The general purpose of the present intergluteal perspiration pad, described subsequently in greater detail, is to provide an intergluteal perspiration pad which has many novel features that result in an intergluteal perspiration pad which is not anticipated, rendered obvious, suggested, or even implied by prior art, either alone or in combination thereof.

To accomplish this, the present intergluteal perspiration pad includes an absorbent pad having a convex top side, a bottom side, a right side and a left side. Thus, the pad is conformed to fit the small of the back at the gluteal cleft. An absorbent cover is continuously disposed on the pad. The cover has a convex upperside, an underside, a U-shaped first end and a U-shaped second end. The cover may be sewn around absorbent pad. The present device has a first attachment member and a second attachment member. The first and second attachment members are U-shaped clips and have internal walls with ridges thereon to secure the device to a waistband. Each of the attachment members slidingly engages one of the first end and the second end thus allowing the present intergluteal perspiration pad to be attached to the waistband of various garments, such as pants, skirts, and shorts, in a position to absorb perspiration from the gluteal cleft.

The pad may be formed of sponge and alternately a spongy material. The pad cover can be made of various absorbent materials to accommodate desired comfort and tactile concern. Thus has been broadly outlined the more important features of the present intergluteal perspiration pad so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
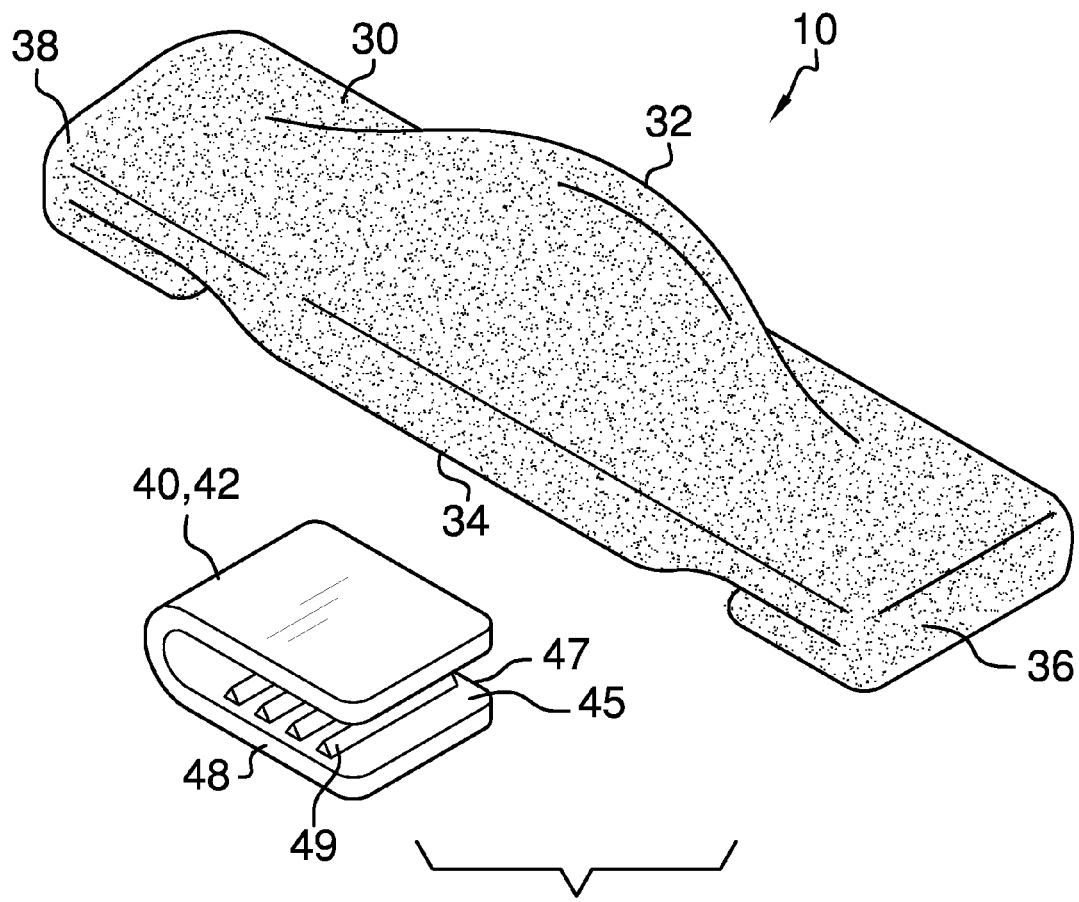
FIG. 1 is an isometric view.
Figure 2:
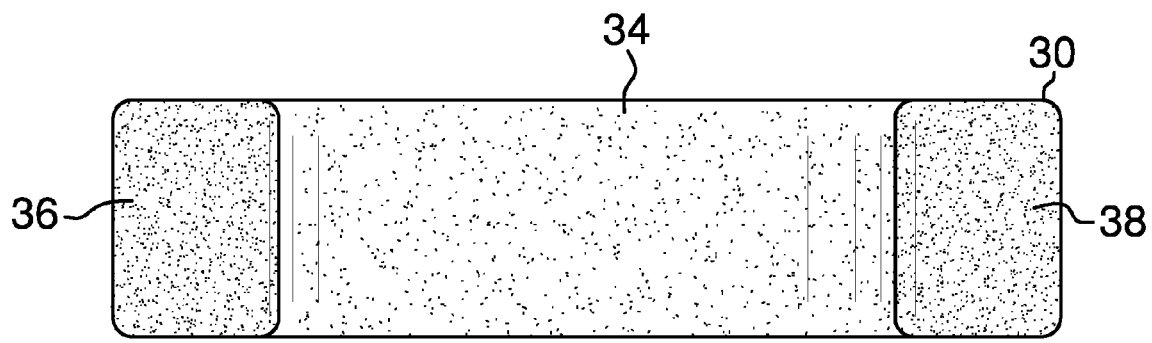
FIG. 2 is a bottom plan view of a cover.
Figure 3:
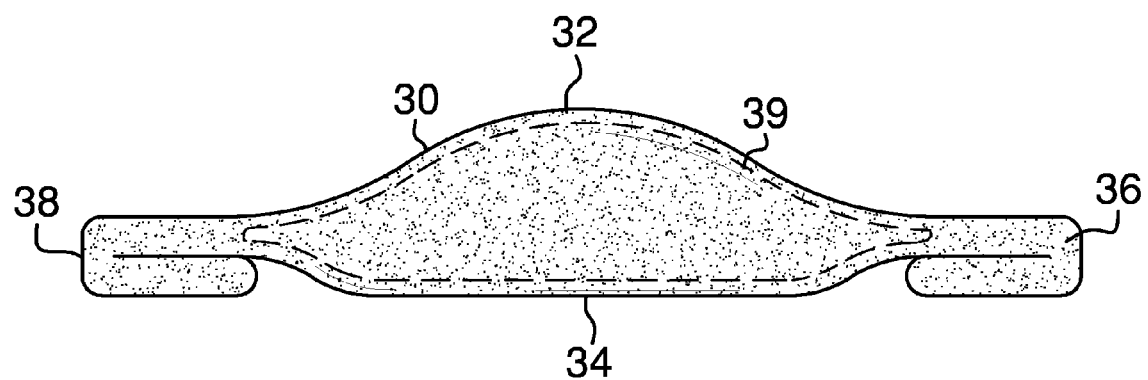
FIG. 3 is a side elevation view of the cover with a partial cutaway showing an absorbent pad inside the cover.
Figure 4:
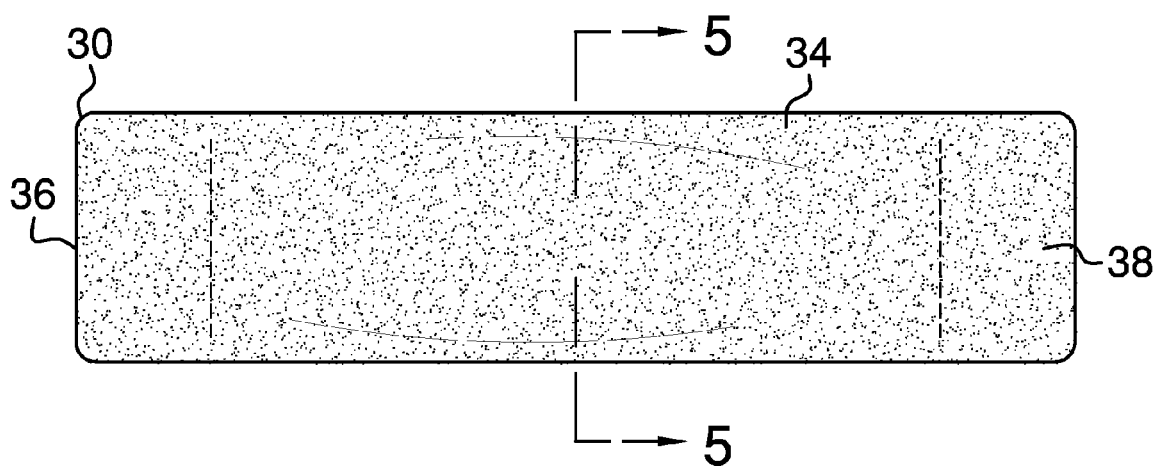
FIG. 4 is a top plan view of the cover.
Figure 5:
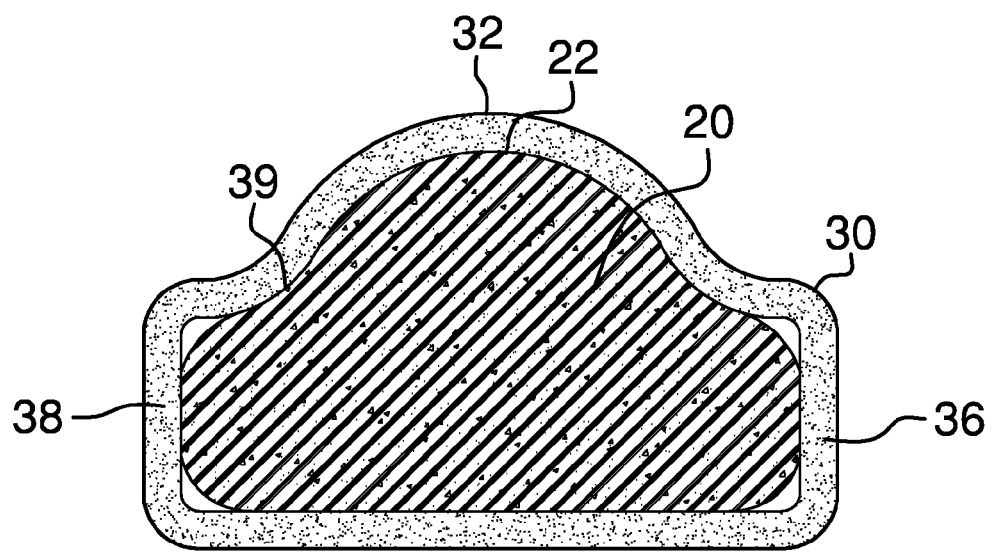
FIG. 5 is a cross-sectional view taken along line 5-5 of FIG. 4.
Figure 6:
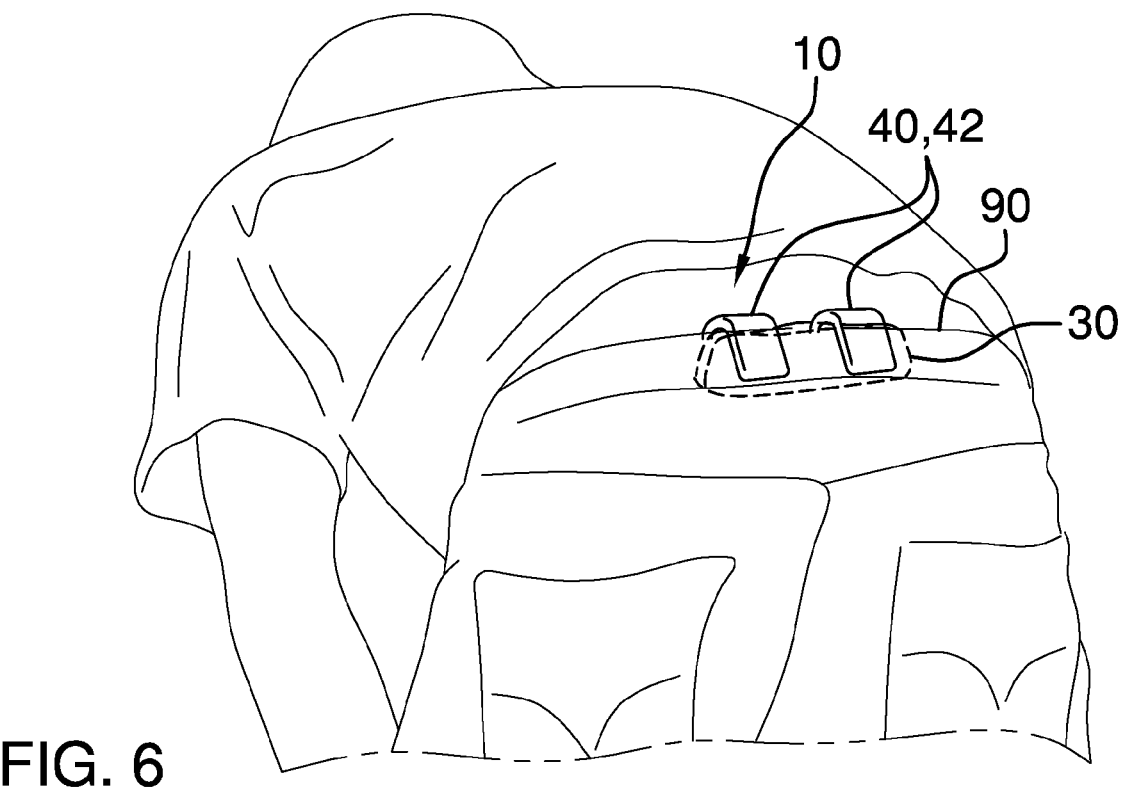
FIG. 6 is an in-use view of the device.

With reference now to the drawings, and in particular FIGS. 1 through 6 thereof, an example of the instant intergluteal perspiration pad employing the principles and concepts of the present intergluteal perspiration pad and generally designated by the reference number 10 will be described.

Referring to FIGS. 1 through 6 a preferred embodiment of the present intergluteal perspiration pad 10 is illustrated. The intergluteal perspiration pad 10 includes an absorbent pad 20. The absorbent pad 20 has a convex top side 22. The top side 22 is convex to conform to fit the small of the back at the gluteal cleft. The intergluteal perspiration pad 10 also includes an absorbent cover 30 continuously disposed upon the pad 20. The cover 30 has a convex upperside 32, an underside 34, a U-shaped first end 36, and a U-shaped second end 38. The cover 30 can be sewn along a seam 39. The pad 20 can be formed of sponge or alternately a spongy material. The intergluteal perspiration pad 10 also includes a first attachment member 40 and a second attachment member 42, which are U-shaped clips. The first attachment member 40 and the second attachment member 42 slidingly engage one of the first end 36 and second end 38 to attach the combined pad 20 and cover 30 to the waistband 90 of various garments such as pants, skirts, and shorts, in a position to absorb perspiration from the gluteal cleft.

Each of the first attachment member 40 and the second attachment member 42 has a continuous interior wall 45. The interior wall 45 has a right side 47 and a left side 48. The first and second attachment members 40, 42 are U-shaped. A plurality of ridges 49 is disposed on the interior wall 45. Each ridge 49 is disposed across the interior wall 45 from the right side 47 to the left side 48. The ridges 49 further assist in securing the combined pad 20 and cover 30 to the waistband 48.

The sponge 20 and the cover 30 have a combined depth in a range of two inches to three inches. In addition, the sponge 20 and the cover 30 have a combined length in a range of eight inches to twelve inches. Also, the sponge 20 and the cover 30 have a combined width in a range of two inches to three inches. The foregoing dimensions permit the present device 10 to optimally perform its functions.

What is claimed is:

1. An intergluteal perspiration pad comprising:
    an absorbent pad having a convex top side;
    a cover continuously disposed on the pad, the cover having a convex upper side, an underside, a U-shaped first end, and a U-shaped second end;
    a first attachment member and a second attachment member slidingly disposed through one of the first end and the second end;
    wherein each of the first attachment member and the second attachment member is configured to attach the pad and the cover thereon to a waistband of a garment;
    a continuous interior wall disposed within each of the first and second attachment members; and
    a plurality of ridges disposed on the interior wall.

2. The intergluteal perspiration pad of claim 1 wherein the cover is absorbent.

3. The intergluteal perspiration pad of claim 2 wherein the pad and the cover have a combined depth in a range of two inches to three inches;

wherein the pad and the cover have a combined length in a range of eight inches to twelve inches; and wherein the pad and the cover have a combined width in a range of two inches to three inches.

4. An intergluteal perspiration pad comprising:

an absorbent pad having a convex top side;

an absorbent cover continuously disposed on the pad, wherein the cover has a convex upper side, an underside, a U-shaped first end, and a U-shaped second end;

a first attachment member and a second attachment member slidingly disposed through one of the first end and the second end, each of the first and second attachment members comprising a U-shaped clip;

a continuous interior wall disposed within each of the first and second attachment members, the interior wall having a right side and a left side;

a plurality of ridges disposed on the interior wall, each ridge disposed across the interior wall from the right side to the left side; and wherein each of the first attachment member and the second attachment member is configured to attach the pad and the cover thereon to a waistband of a garment.

5. The intergluteal perspiration pad of claim 4 wherein the pad and the cover have a combined depth in a range of two inches to three inches, a combined length in a range of eight inches to twelve inches, and a combined width in a range of two inches to three inches.

\* \* \* \* \*